United States Patent [19]
Yeo

[11] Patent Number: 5,533,990
[45] Date of Patent: Jul. 9, 1996

[54] TAMPON EXHIBITING LOW FRICTIONAL DRAG

[75] Inventor: Richard S. Yeo, Dunwoody, Ga.

[73] Assignee: Kimberly-Clark Corporation, Neenah, Wis.

[21] Appl. No.: 311,692

[22] Filed: Sep. 23, 1994

[51] Int. Cl.⁶ .................................................. A61F 13/20
[52] U.S. Cl. ...................... 604/363; 604/12; 604/904
[58] Field of Search ........................ 604/12, 15, 358, 604/363, 365, 904

[56] References Cited

U.S. PATENT DOCUMENTS

| | | |
|---|---|---|
| 2,849,000 | 8/1958 | Lewing . |
| 3,595,236 | 7/1971 | Corrigan .................. 604/363 |
| 3,796,219 | 3/1974 | Hanke . |
| 4,300,561 | 11/1981 | Kaczmarzyk et al. .................. 604/363 |
| 4,312,348 | 1/1982 | Friese . |
| 4,377,167 | 3/1983 | Kaczmarzyk et al. . |
| 4,428,747 | 1/1984 | Friese et al. .............................. 604/12 |
| 4,951,368 | 8/1990 | Heinen ...................... 28/118 |
| 5,073,365 | 12/1991 | Katz et al. ................. 604/265 |
| 5,084,038 | 1/1992 | Sheldon et al. .......................... 604/358 |
| 5,153,971 | 10/1992 | Van Iten ...................... 28/118 |
| 5,158,535 | 10/1992 | Paul et al. .................................. 604/15 |
| 5,185,010 | 2/1993 | Brown, Jr. .............................. 604/379 |
| 5,342,335 | 8/1994 | Rhim ...................... 604/367 |

FOREIGN PATENT DOCUMENTS 861154  1/1971  Canada ...................................... 2/115

Primary Examiner—David Isabella
Assistant Examiner—Laura Fossum
Attorney, Agent, or Firm—Thomas J. Connelly

[57] ABSTRACT

A tampon is disclosed which exhibits low frictional drag during insertion into and withdrawal from a woman's vagina. The tampon includes an absorbent compressed into a generally cylindrical shape and a liquid-permeable cover which surrounds at least a portion of the absorbent. The cover is treated with an aqueous solution having a viscosity of at least 50 cps at a temperature of about 25° C. The solution includes a lubricant and at least about 3 percent by weight of a polymer. The polymer serving to prevent the lubricant from migrating away from the cover such that the tampon retains a sufficient amount of lubricant to facilitate comfortable withdrawal from the vaginal cavity.

19 Claims, 1 Drawing Sheet

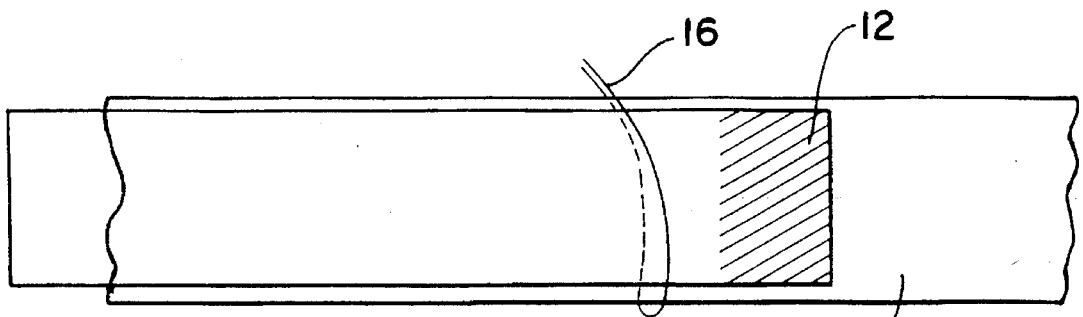
FIG. 1
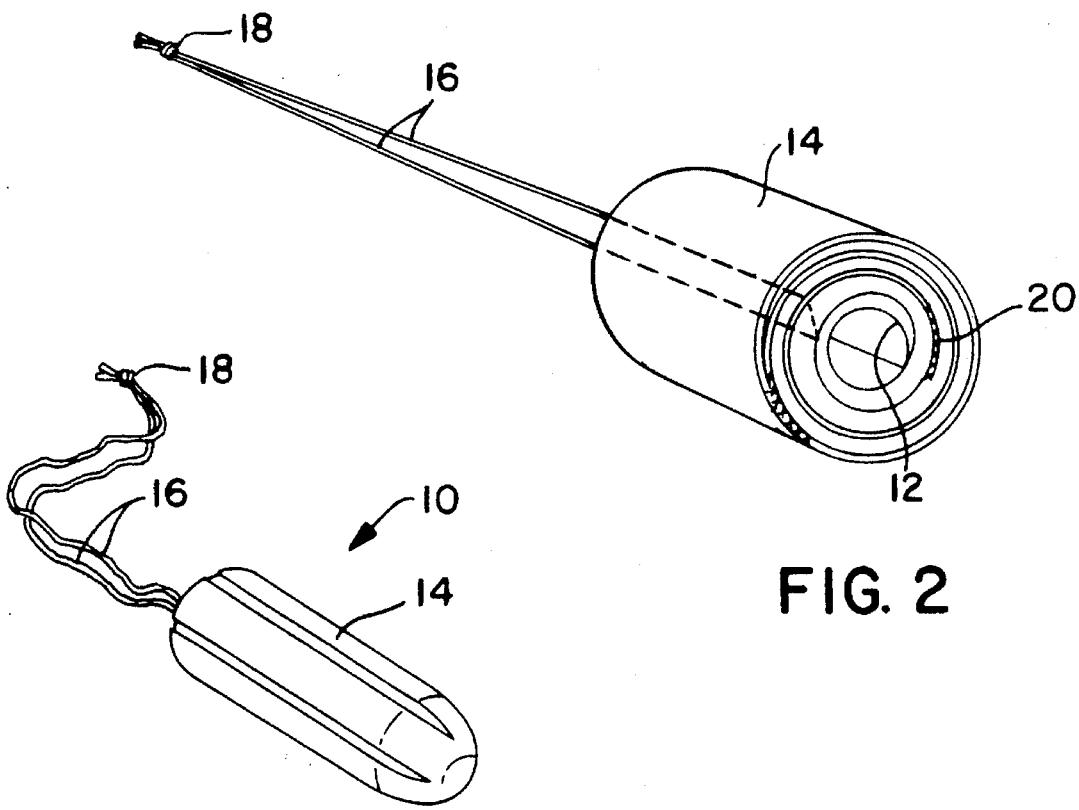
FIG. 2
FIG. 3
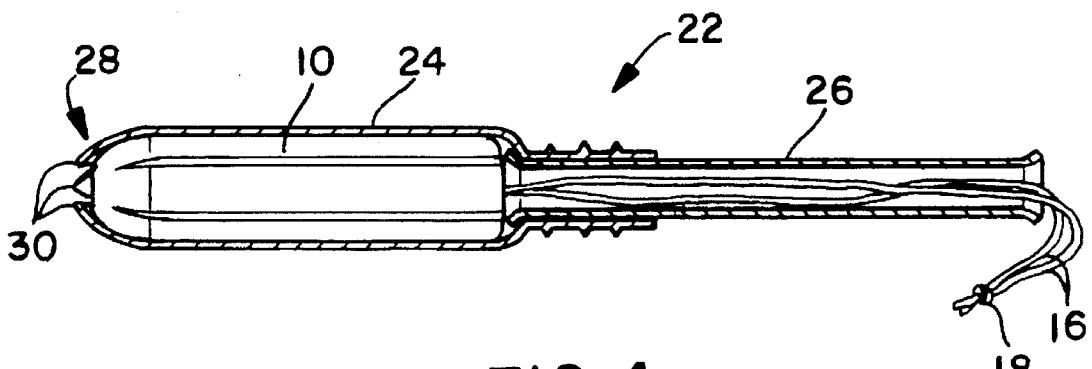
FIG. 4

TAMPON EXHIBITING LOW FRICTIONAL DRAG

FIELD OF THE INVENTION

This invention relates to a tampon which exhibits low frictional drag during insertion into and withdrawal from a woman's vagina. More particularly, this invention relates to a tampon having a cover which is treated with an aqueous solution including a lubricant and a polymer.

BACKGROUND OF THE INVENTION

Catamenial tampons are internal protection devices which have been used for years for absorbing menses, blood and other body fluid. Tampons are normally used during a woman's menstrual period to prevent leakage of menstrual fluid. A tampon includes an absorbent material, such as cotton, rayon, cellulose wadding, synthetic sponge, cellulose fluff, synthetic fibers, or combinations thereof, which is compressed into a generally cylindrical shape. The cylindrically shaped absorbent material is usually surrounded by a liquid-permeable cover. Catamenial tampons are available in a variety of sizes and shapes so as to accommodate different size vaginal cavities.

The tampons are sufficiently compressed to retain their size and shape under normal atmospheric conditions but are designed to expand readily when wetted by body fluid. For example, after a tampon is inserted into a woman's vaginal tract and is contacted by body fluid, the compressed tampon attempts to re-expand approximately to it's original uncompressed size. This structural change allows the tampon to fill the vaginal cavity and absorb body fluid thereby preventing leakage. This enlargement can cause discomfort during withdrawal of the tampon from the vaginal cavity if proper lubrication is not present.

With the popularity of tampon applicators on the rise, most women do not experience discomfort during the insertion of a tampon into their vaginal tract. This is because the outer tube of a tampon applicator is either made from a coated paper or from a smooth plastic material which slides along the walls of the vagina with a minimum amount of frictional drag. However, during withdrawal of the expanded tampon from the vaginal cavity, a woman may experience discomfort. Manufacturers have attempted to correct this problem by coating the outside absorbent fibers of the tampon with a lubricant. A lubricant will definitely reduce the drag resistance during withdrawal. However, it has been found that many lubricants tend to migrate onto and/or into surrounding materials such as the packaging and/or the absorbent fibers prior to use. When this occurs, the lubricant is not present in a sufficient amount on the surface of the tampon to facilitate comfortable withdrawal from the vaginal cavity. Furthermore, some lubricants tend to migrate into the absorbent fibers and decrease their absorption and retention properties.

In view of the above, there is a need for a tampon which exhibits low frictional drag during insertion into and especially withdrawal from a woman's vagina so as to improve comfort.

SUMMARY OF THE INVENTION

Briefly, this invention relates to a tampon exhibiting low frictional drag during insertion into and withdrawal from a woman's vagina. The tampon includes an absorbent compressed into a generally cylindrical shape and a liquid-permeable cover which surrounds at least a portion of the absorbent. The cover is treated with an aqueous solution having a viscosity of at least 50 cps at a temperature of about 25° C. The solution includes a lubricant and at least about 3 percent by weight of a polymer. The polymer serves to prevent the lubricant from migrating away from the cover such that the tampon retains a sufficient amount of lubricant to facilitate comfortable insertion into and withdrawal from the vaginal cavity.

The general object of this invention is to provide a tampon which exhibits low frictional drag during insertion into and withdrawal from a woman's vagina. A more specific object of this invention is to provide a tampon having a cover treated with an aqueous solution including a lubricant and a polymer.

Another object of this invention is to provide a tampon with a cover which has been treated with an aqueous solution having a viscosity of at least 50 cps at a temperature of about 25° C.

A further object of this invention is to provide a tampon which exhibits improved circumferential fluid staining.

Still another object of this invention is to provide a tampon which exhibits improved circumferential wicking properties.

Still another object of this invention is to provide a tampon with improved tear strength.

Still further, an object of this invention is to provide a tampon which exhibits less linting problems.

Other objects and advantages of the present invention will become more apparent to those skilled in the art in view of the following description and the accompanying drawings.

BRIEF DESCRIPTION OF THE DRAWINGS

FIG. 1 is a top view of an absorbent ribbon positioned above a liquid-permeable cover.

FIG. 2 is a perspective view of a "softwind" containing a cover which has been treated with an aqueous solution containing a lubricant and a polymer.

FIG. 3 is a perspective view of a catamenial tampon having a compressed absorbent enclosed by a cover which has been treated with an aqueous solution containing a lubricant and a polymer.

FIG. 4 is a cross-sectional view of a tampon positioned in a tampon applicator.

DETAILED DESCRIPTION OF THE PREFERRED EMBODIMENT

Referring to FIGS. 1–3, the construction of a catamenial tampon 10 is shown which exhibits low frictional drag during insertion into and withdrawal from a woman's vagina. The tampon 10 includes an absorbent 12 which has been compressed into a generally cylindrical shape and a liquid-permeable cover 14 which surrounds or encloses at least a portion of the absorbent 12. The tampon 10 can be constructed by positioning the absorbent 12 on the cover 14, as indicated in FIG. 1, and then rolling the two layers, in direction A, into a generally cylindrical shape. This uncompressed cylindrical shape, shown in FIG. 2, is known as a "softwind." The softwind is then compressed into a tampon pledget as is shown in FIG. 3. It should be noted that it is also possible to first roll the absorbent 12 into a generally cylindrical shape and then wrap the liquid-permeable cover 14 around it. It is also possible to roll up and compress the absorbent 12 before wrapping it in the cover 14.

Referring to FIG. 3, the tampon 10 further includes a withdrawal string 16 which is secured to either the absorbent 12, the cover 14 or to both and provides a safe and reliable means by which the tampon 10 can be withdrawn from a woman's vagina after it has absorbed a certain amount of menstrual fluid. The withdrawal string 16 can be assembled with the softwind, as depicted in FIG. 1, or it can be attached to the compressed pledget, depending upon one's preference. In either case, the free end of the withdrawal string 16 is tied in a knot 18 to assure that it will not be separated from the pledget.

The absorbent 12 can be formed from absorbent fibers which are first assembled into an absorbent ribbon or sheet. Alternatively, the absorbent 12 can be formed from absorbent fibers which are assembled and compressed into a generally cylindrical configuration. The absorbent 12 is preferably formed from cellulosic fibers, such as cotton and rayon. The absorbent can be 100% cotton, 100% rayon, or a blend of both cotton and rayon. A ratio of from about 15% cotton and about 85% rayon works well. The particular blend of fibers can vary depending on one's preference.

The cotton fibers should have a staple length of between about 5 mm to about 20 mm. The fibers can be bleached if desired. Bleaching will make the fibers whiter in appearance. The cotton should generally have a fiber size of between about 150 to about 280 microns.

The rayon fibers should have a staple length of between about 20 mm to about 35 mm. The fibers can also be bleached if desired. The rayon fibers should have a denier of between about 25 to about 28. Denier is a unit of fineness of yarn based on a standard of 50 milligrams per 450 meters of yarn.

The absorbent 12, when formed from an absorbent ribbon, is constructed from a blend of rayon and cotton fibers in a process known to those skilled in the art as "carding." Depending upon the desired absorbency one desires in the finished tampon, the basis weight of the absorbent ribbon can vary. The U.S. Food and Drug Administration (FDA) has set absorbency standards for "regular," "super" and "super-plus" size tampons. In order to meet these standards for the three above-identified sizes, the absorbent ribbons are targeted to have basis weights of about 127 grams per square meter (gsm), 170 gsm and 230 gsm, respectively. Typically, the carding process is controlled to produce an absorbent ribbon with a width of about 50 mm for a "regular" size tampon and a width of about 55 mm for both the "super" and "super-plus" size tampons. During the assembly process, one end of the rectangular absorbent ribbon having a length of about 300 mm is positioned over a portion of the cover 14. The two materials are then rolled up into a generally cylindrically shape. This action will cause the absorbent 12 to be located on the interior and be surrounded by the cover 14. The cover 14 will surround the exterior surface of the softwind and can overlap upon itself, if desired.

The cover 14 can be bonded, as indicated by numeral 20, to itself and/or to the absorbent ribbon 12 using heat, pressure or a combination of heat and pressure. The softwind is then compressed into a finished tampon pledget 10. Preferably, the bonding 20 will occur during the compression step.

The cover 14 can be formed from woven or nonwoven materials having a porous substrate. Woven materials include textile fabrics and nonwoven materials include spunbond and bonded carded webs. Both of these nonwoven materials are commercially sold by Kimberly-Clark Corporation, 401 N. Lake Street, Neenah, Wis. 54956. Another nonwoven material which can be used as the cover 14 is formed from 100 percent polyester fibers held together by a binder. This material is known as powder-bonded-carded web (PBCW) and is also available from Kimberly-Clark Corporation.

The withdrawal string 16 can be constructed from various types of threads or ribbons. A thread made from 100 percent cotton fibers works well. The withdrawal string 16 normally has a length extending beyond one end of the tampon 10 from about 2 inches to about 8 inches (about 50.8 mm to about 203.2 mm), preferably from about 4 inches to about 6 inches (about 102 mm to about 152.4 mm), and most preferably, about 5 inches (127 mm). The withdrawal string 16 can be dyed and treated with an anti-wicking agent, such as wax, before being secured to the softwind or pledget to prevent it from wicking menstrual fluid. A dry, clean withdrawal string 16 is preferred by the user when she goes to remove the tampon 10. The liquid-permeable cover 14 is treated by an aqueous solution to reduce frictional drag, to give it permanent wettability and to enhance ease of insertion into and withdrawal from a vaginal cavity. The cover 14 can be treated either before being rolled up with the absorbent 12 or after being wrapped around the absorbent 12. The aqueous solution contains water, a lubricant and a polymer. The aqueous solution should have a viscosity of at least 50 centipoise (cps) at a temperature of about 25° C. A low viscosity, under 50 cps at a temperature of about 25° C., will not allow a constant and uniform coating of the solution to be applied to the cover 14. The proper viscosity for the aqueous solution assures that a constant and uniform coating can be applied to the cover 14, that the solution is stable and has good adhesion properties. The polymer should also exhibit film forming properties so as to enable it to be uniformly coated onto the cover 14.

The aqueous solution can contain any kind of water, such as distilled water, deionized water, tap water, etc. Distilled water is preferred because of it's purity.

The lubricant present in the aqueous solution must be safe for use with the human body. A preferred lubricant is myreth-3-myristate, which is commercially sold under the Trademark Cetiol® 1414-E by Henkel Incorporated, 1301 Jefferson Street, Hoboken, N.J. 07030. Myreth-3-myristate has a cloud point which ranges between about 20° C. to about 25° C. Myreth-3-myristate is an oily liquid at a temperature above it's cloud point. When the myreth-3-myristate is below it's cloud point, it starts to crystalize. Myreth-3-myristate is insoluble but dispersible in water. Myreth-3-myristate is also insoluble in body fluids, especially menstrual fluid. The lubricant can represent from between about 5 percent to about 60 percent by weight of the aqueous solution. The ratio of the concentration of lubricant to polymer in the aqueous solution should be at least about 2:1 and, preferably, about 4:1.

The presence of a polymer in the aqueous solution reduces the potential migration of the lubricant from the cover 14 of the tampon 10. The polymer attracts and holds the lubricant thereby preventing it's migration. By retaining the lubricant on the outside surface of the cover 14, the tampon 10 will experience a low frictional drag, especially during withdrawal from the vagina. Without the polymer, the lubricant, especially myreth-3-myristate, has a high affinity to migrate into or onto other materials which it comes in contact with. This affinity is due to the compatibility of the lubricant for many materials. For example, if the lubricant was coated on the cover 14 without the polymer, it would have a tendency to migrate to the absorbent fibers themselves or to the packaging material in which the tampon is wrapped. When this occurs, it has been found that an ineffective amount of lubricant remains on the exterior surface of the tampon 10. Without sufficient lubricant being present on the cover 14, the user may experience discomfort as she attempts to withdraw the swollen and soiled tampon 10 from her vagina.

The polymer present in the aqueous solution should be water based and have a good adhesion to the fiber/web surface of the absorbent 12. In addition, the polymer is preferably insoluble in body fluids such as menstrual or vaginal fluids at a body temperature of about 37° C. Various polymers which can be used in the aqueous solution include polyvinyl alcohol, starches and latices. Polyvinyl alcohol has been found to be particularly useful and is preferred.

It should be noted that there are numerous grades of polyvinyl alcohols, many of which have different solubility characteristics in water. For example, some grades are soluble in water at ambient temperature while others are soluble in water only at elevated temperatures. However, for purposes of this invention, there are no known limitations with respect to the grade or nature of the polyvinyl alcohol which can be used in the aqueous solution.

The polymer should have a relatively high degree of hydrolysis, preferably, it should completely insoluble in water at body temperature. Hydrolysis is the process whereby, for example, an acetate side chain on the polymer is hydrolyzed to a hydroxyl group. This is required since the polymer does not require the use of a cross-linking agent and will not dissolve in menstrual fluid, vaginal fluid or other types of body fluids. When the polymer is polyvinyl alcohol, the degree of hydrolysis should be between about 97 percent to about 99 percent and the polyvinyl alcohol should be soluble in water at a temperature above 80° C. Polyvinyl alcohol is soluble in water at any temperature if the hydrolysis is around 87 percent.

The polymer can be made to have different molecular weights. However, in order to assure that the aqueous solution has a sufficient viscosity, the polymer must have a certain molecular weight in combination with it's concentration. Molecular weight is defined by the American Heritage Dictionary, Second College Edition, 1985, on page 808, as "the sum of the atomic weights of a molecule's constituent atoms" and is normally defined in grams/mole. When the polymer has a relatively low molecular weight, of from between about 11,000 to about 31,000, the concentration should be between about 5 to about 15 percent by weight in order for the aqueous solution to have sufficient viscosity. When the polymer has a relatively high molecular weight of from between about 106,000 to about 110,000, the concentration should be between about 3 to about 10 percent by weight. In general, as the molecular weight of the polymer is increased, the concentration can decrease.

If the concentration of the polymer is too low, the polymer becomes ineffective in providing a means by which a constant amount of the lubricant can be coated onto the cover 14 in a continuous coating operation. When the concentration of the polymer is too high, all of the polymer may not dissolve in the water at ambient temperature and the amount of coating on the cover is too high and this means that one is wasting coating material. Since the lubricant is rather expensive compared to the other constituents of the aqueous solution, one should avoid using a higher concentrate solution than absolutely required. For example, when one uses a polymer having a relatively high molecular weight in the range of about 106,000 to about 110,000 and a concentration above 12 percent, one will find that some of the polymer may not dissolve in the water and therefore, the cost of the aqueous solution will increase without added benefit. This effect is not cost effective and should be avoided.

It should be noted that the entire exterior surface of the cover 14 should be coated with a uniform amount of the aqueous solution in order to provide a low frictional drag during insertion and withdrawal into and out of the vaginal cavity. The aqueous solution should be applied to the cover 14 in a liquid state and allowed to dry. As the water evaporates, the polymer will turn into a solid. The aqueous solution should not interfere with the ability of the tampon 10 to absorb menstrual and other body fluids. The aqueous solution also should not restrict the ability of the cover 14 to expand as the absorbent 12 swells in size as it collects and retains menstrual fluid.

The presence of a uniform coating is also beneficial in that it will allow the circumference of the tampon 10 to exhibit a continuous menstrual stain. The presence of a menstrual stain over a substantial portion of the exterior surface of the cover 14, once the tampon 10 is withdrawn from the vaginal cavity, is important because it provides a visual signal to the consumer. The consumer equates a large stain area as showing that the tampon 10 has functioned extremely well in blocking and collecting menstrual fluid, blood and other body fluids during her menstrual period. If a stain occupies a small area or is not present at all, some consumers assume that the tampon was ineffective and will tend to use a different brand of tampon or may switch to an external sanitary napkin.

Since the cover 14 has to be both soft and flexible as well as being capable of expanding as the absorbent 12 expands with the intake of body fluids, it may be advantageous to add a plasticizer to the aqueous solution. Suitable plasticizers can include any of the known plasticizers, such as glycerol, ethylene glycol, propylene glycol, polyethylene glycol, etc. Glycerol has been found to be a particularly useful plasticizer for polyvinyl alcohol because it keeps the coating soft and retains moisture. The plasticizer can be added to the aqueous solution in an amount of from between about 0.1 percent to about 5 percent by weight, preferably, less than about 2 percent by weight. Some plasticizers, especially glycerol, have a high surface tension and this cooperates with the lubricant to enhance the wicking performance of the cover 14. This wicking capability facilitates movement of the body fluid into the absorbent.

The following examples further describe and demonstrate the present invention. The examples are given solely for the purpose of illustration and are not to be construed as limitations, as many variations are possible without departing from the spirit and scope of the present invention.

EXAMPLE 1

Aqueous solutions of and polyvinyl alcohol (Airvol™ 165) having a relatively high molecular weight (106,000–110,000) were prepared in polymer concentrations, without Cetiol™, of 1 percent, 2 percent, 3 percent and 4 percent. The polyvinyl alcohol solutions were then mixed with a lubricant (Cetiol™ 1414-E) so that the aqueous solutions contained a lubricant/polymer ratio of about 4:1. Samples of spunbond webs, having a dimension of about 8 inches by about 10 inches (about 203.2 by about 254.0 mm) and a basis weight of 0.4 ounces per square yard (osy), were dipped into a bath of the aqueous solution. The webs were then fed through a nip roll to remove excess solution. The samples were then allowed to dry at room temperature overnight. Each spunbond web was treated separately and the webs were numbered 1–12 according to the sequence of treatment. The add-on level of the subsequent pieces was normalized with reference to the first piece. The results were as follows:

| Sample # | 1% | 2% | 3% | 4% |
|---|---|---|---|---|
| 1 | 1.00 | 1.00 | 1.00 | 1.00 |
| 2 | 0.546 | 0.786 | 0.886 | 0.912 |
| 3 | 0.382 | 0.674 | 0.871 | 0.840 |
| 4 | 0.330 | 0.661 | 0.863 | 0.877 |
| 5 | 0.285 | 0.538 | 0.786 | 0.856 |
| 6 | 0.289 | 0.544 | 0.841 | 0.807 |
| 7 | 0.272 | 0.531 | 0.859 | 0.917 |
| 8 | 0.268 | 0.464 | 0.813 | 0.851 |
| 9 | 0.235 | 0.425 | 0.818 | 0.861 |
| 10 | 0.259 | 0.419 | 0.759 | 0.884 |
| 11 | 0.211 | 0.415 | — | 0.923 |
| 12 | — | 0.362 | — | 0.867 |
| Viscosity of PVOH (cps) | 11.1 | 23.6 | 38.0 | 84.8 |
| Viscosity of aqueous solution (cps) | 18 | 28.6 | 53.6 | 109.2 |

The viscosity of the aqueous solution was measured at 100 revolutions per minute (rpm) by using a viscometer supplied by Brookfield Engineering Laboratories, Inc. of Stoughton, Mass.

The above data indicates that the viscosity of the aqueous solution has a major impact on the ability to uniformly coat the spunbond web at a constant add-on level. At 1 percent, each subsequent web which entered the aqueous bath was coated with less polyvinyl alcohol and Cetiol™. The eleventh sample at 1 percent contained only 0.211 of the amount of polyvinyl alcohol and Cetiol™ present on the first sample. In summary, the polyvinyl alcohol and Cetiol™ in the aqueous solution was diminishing as additional sample webs went through the bath. At 2 percent, the twelfth sample only contained 0.362 of the amount of polyvinyl alcohol and Cetiol™ present on the first sample at 2 percent. At 3 percent, the tenth sample contained 0.759 of the amount of polyvinyl alcohol and Cetiol™ present on the first sample at 3 percent. This is good for it meant that the polymer and lubricant were remaining in the bath and that subsequent webs could be treated and would contain an adequate amount of polymer and lubricant. The results at 4 percent were even better for the twelfth sample contained 0.867 of the amount of polyvinyl alcohol and Cetiol™ present on the first sample at 4 percent.

EXAMPLE 2

Frictional force measurements were performed to show that the presence of the aqueous solution on the cover would reduce the frictional drag better than if the cover was untreated or simply treated with a lubricant. The tests performed were as follows:

An untreated 0.4 osy spunbond web was placed on a Lucite plate. Another Lucite plate of 5" by 6" was placed on the spunbond sample. The sample along with the two Lucite plates was subjected to a pressure of 0.09 psi. The sample was then pulled on one side and the required force was measured with a Chatilon Digital Force Gauge DFI 50 supplied by S. A. Meier Co., Inc. of Milwaukee, Wis. The required force for the untreated spunbond web was 1.75 lb.

A 0.5 osy spunbond web was treated with an aqueous solution containing 133 grams of water, 16 grams of lubricant (Cetiol™) and 4 grams of polyvinyl alcohol (Airvol™ 165), commercially available from Air Products and Chemicals, Co. of Allentown, Pa. The add-on of the treated spunbond web was 50.6 weight percent. The test described above was performed on this treated web. The required force was 0.80 lb.

A 0.4 osy spunbond web was treated with an aqueous solution containing 396 grams of water, 14.3 grams of lubricant (Cetiol™) but no polyvinyl alcohol. The add-on of the treated spunbond web was 41.6 weight percent. The test described above was performed on this treated web. The required force was 0.85 lb.

The results from these three measurements clearly show that the spunbond web treated with the aqueous solution containing the polymer required the lowest pulling force. Therefore, a tampon having this aqueous solution coated on it's cover would require less force to insert and/or remove the tampon from a vaginal cavity.

EXAMPLE 3

Two tests were conducted to determine if the polymer acted to prevent the loss of lubricant from a spunbond web. The tests performed were as follows:

A 0.4 osy spunbond web was treated with a solution containing 396 grams of water and 14.3 gram of Cetiol™. The add-on of the treated web was 41.6 weight percent. The treated web was placed between two sheets of paper towel. A pressure of 0.2 psi was placed on the top paper towel. After 5 minutes, the pressure was withdrawn and the treated web was removed from between the two sheets of paper towel. The add-on level of the spunbond web was determined to be 11.9 weight percent. This represented a decrease of 29.7 percent. The spunbond web was then subjected to the pulling test described in Example 2. The required force was 1.05 lb.

A 0.4 osy spunbond web was treated with an aqueous solution containing 125 grams of water, 10 grams of Cetiol™ and 2.5 grams of polyvinyl alcohol (Airvol™ 165), commercially available from Air Products and Chemicals, Co. of Allentown, Pa. The add-on of the treated web was 41.1 percent. The treated spunbond web was placed between two sheets of paper towel. A pressure of 0.2 psi was placed on the top paper towel. After 5 minutes, the pressure was withdrawn and the treated web was removed from between the two sheets of paper towel. The add-on level of the web was determined to be 34.8 percent. This represented a decrease of 6.3 percent. The spunbond web was then subjected to the pulling test described in Example 2. The required force was 0.85 lb.

These tests conclude that the presence of the polyvinyl alcohol plays a significant role in preventing the loss of the lubricant from the web.

Referring to FIG. 4, a tampon applicator 22 is depicted which includes an outer tube 24 and an inner tube 26. The inner tube 26 is telescopically slidable in the outer tube 24. The outer tube 24 has a forward insertion end 28 with a plurality of petals 30 formed thereon. The tampon 10 is positioned in the outer tube 24 and is capable of being expelled therefrom by movement of the inner tube 26 into the outer tube 24. As the tampon 10 is pushed forward against the petals 30, they will radially open to allow the tampon 10 to pass through. When a woman uses a tampon applicator 22 to properly position the tampon 10 into her vagina, the need for the aqueous solution on the cover 14 of the tampon 10 is still important. The reason for this is that the aqueous solution should be present to assist with the withdrawal of the swollen tampon 10 from her vagina.

When the tampon 10 is inserted without the aid of an applicator, the aqueous solution becomes important during both the insertion process and during withdrawal.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A tampon exhibiting low frictional drag comprising:
   a) a compressed absorbent; and
   b) a cover surrounding at least a portion of said absorbent, said cover being treated with an aqueous solution having a viscosity of at least 50 cps at a temperature of about 25° C., said solution including a lubricant and polyvinyl alcohol, said polyvinyl alcohol preventing said lubricant from migrating away from said cover.

2. The tampon of claim 1 wherein said polyvinyl alcohol is present in said aqueous solution in a concentration of from between about 3 percent to about 10 percent by weight and has a molecular weight of at least about 106,000.

3. The tampon of claim 1 wherein said polyvinyl alcohol is present in said aqueous solution in a concentration of from between about 5 percent to about 15 percent by weight and has a molecular weight of at least about 11,000.

4. The tampon of claim 1 wherein said lubricant is myreth-3-myristate.

5. The tampon of claim 4 wherein said myreth-3-myristate is present in said aqueous solution in a concentration of between about 5 to about 60 percent by weight.

6. A tampon exhibiting low frictional drag comprising:
   a) an absorbent compressed into a generally cylindrical shape;
   b) a liquid-permeable cover surrounding at least a portion of said absorbent, said cover being treated with an aqueous solution having a viscosity of at least 50 cps at a temperature of about 25° C., said solution including a lubricant and at least about 3 percent of polyvinyl alcohol, said polyvinyl alcohol preventing said lubricant from migrating away from said cover; and
   c) withdrawal means for removing said tampon from a woman's vagina, said withdrawal means being attached to said absorbent.

7. The tampon of claim 6 wherein said polyvinyl alcohol is present in said aqueous solution in a concentration of from between about 3 to about 10 percent by weight and has a molecular weight of at least about 106,000.

8. The tampon of claim 7 wherein said polyvinyl alcohol has a molecular weight of between about 106,000 to about 110,000.

9. The tampon of claim 6 wherein said polyvinyl alcohol is present in said aqueous solution in a concentration of from between about 5 to about 15 percent by weight and has a molecular weight of between about 11,000 to about 31,000.

10. The tampon of claim 6 wherein said lubricant is myreth-3-myristate.

11. A tampon exhibiting low frictional drag during withdrawal from a woman's vagina, said tampon comprising:
    a) an absorbent compressed into a generally cylindrical shape;
    b) a liquid-permeable cover circumferentially surrounding said absorbent, said cover being treated with an aqueous solution having viscosity of at least 50 cps at a temperature of about 25° C., said solution including a lubricant and at least 3 percent by weight of a polymer having a molecular weight of at least 106,000, said polymer preventing said lubricant from migrating away from said cover; and
    c) withdrawal means for removing said tampon from said vagina, said withdrawal means being attached to said absorbent.

12. The tampon of claim 11 wherein said cover is made from a porous substrate.

13. The tampon of claim 12 wherein said cover is a nonwoven.

14. The tampon of claim 12 wherein said cover is spunbond.

15. The tampon of claim 13 wherein said cover is a bonded carded web.

16. A tampon exhibiting low frictional drag during withdrawal from a woman's vagina, said tampon comprising:
    a) an absorbent compressed into a generally cylindrical shape;
    b) a liquid-permeable cover circumferentially surrounding said absorbent, said cover being treated with an aqueous solution having a viscosity of at least 50 cps at a temperature of about 25° C., said solution including myreth-3-myristate and from between about 3 percent to about 10 percent by weight of polyvinyl alcohol having a molecular weight of at least 106,000, said polyvinyl alcohol preventing said myreth-3-myristate from migrating away from said cover; and
    c) withdrawal means for removing said tampon from said vagina, said withdrawal means being attached to said absorbent.

17. The tampon of claim 16 wherein said aqueous solution contains a plasticizer.

18. The tampon of claim 17 wherein said plasticizer is glycerol.

19. The tampon of claim 16 wherein said polyvinyl alcohol has a degree of hydrolysis of between about 97 percent to about 99 percent and is soluble in water at a temperature above 80° C.

* * * * *